US008695594B2

(12) United States Patent
Tham et al.

(10) Patent No.: US 8,695,594 B2
(45) Date of Patent: Apr. 15, 2014

(54) SYSTEM AND METHOD OF AUTOMATED LUNG RECRUITMENT MANEUVERS

(75) Inventors: Robert Q. Tham, Middleton, WI (US); Jaron M. Acker, Madison, WI (US); Gary J. Choncholas, Madison, WI (US); John R. Pinkert, Madison, WI (US)

(73) Assignee: General Electric Company, Schenectady, NY (US)

( * ) Notice: Subject to any disclaimer, the term of this patent is extended or adjusted under 35 U.S.C. 154(b) by 461 days.

(21) Appl. No.: 12/961,051

(22) Filed: Dec. 6, 2010

(65) Prior Publication Data

US 2012/0138057 A1 Jun. 7, 2012

(51) Int. Cl.
*A61M 16/00* (2006.01)
*A61B 5/08* (2006.01)

(52) U.S. Cl.
USPC ..................................... 128/204.23; 600/529

(58) Field of Classification Search
USPC ............. 128/200.24, 204.21, 204.23, 204.24; 600/484, 529–543
See application file for complete search history.

(56) References Cited

U.S. PATENT DOCUMENTS

| | | | |
|---|---|---|---|
| 4,220,160 A | 9/1980 | Kimball et al. | |
| 5,915,381 A * | 6/1999 | Nord | 128/204.23 |
| 6,463,930 B2 | 10/2002 | Biondi et al. | |
| 6,533,730 B2 * | 3/2003 | Strom | 600/533 |
| 6,566,833 B2 * | 5/2003 | Bartlett | 318/564 |
| 6,643,124 B1 | 11/2003 | Wilk | |
| 6,951,541 B2 | 10/2005 | Desmarais | |
| 7,122,010 B2 * | 10/2006 | Bohm et al. | 600/536 |
| 2001/0035186 A1 | 11/2001 | Hill | |
| 2002/0193699 A1 * | 12/2002 | Blomberg | 600/532 |
| 2003/0045807 A1 | 3/2003 | Daniels, II et al. | |
| 2003/0128816 A1 | 7/2003 | Lumbroso et al. | |

(Continued)

FOREIGN PATENT DOCUMENTS

WO  WO 2011045735 A1 * 4/2011

OTHER PUBLICATIONS

Search Report and Written Opinion from corresponding EP Application No. 11191044.4, dated Mar. 19, 2012.

(Continued)

*Primary Examiner* — Annette F Dixon
*Assistant Examiner* — Gregory Winter
(74) *Attorney, Agent, or Firm* — Andrus Intellectual Property Law, LLP

(57) ABSTRACT

A method of providing a recruitment procedure to a patient includes monitoring at least one derecruitment event. A score is calculated for the at least one derecruitment event. A derecruitment score is aggregated. The derecruitment score is compared to a recruitment threshold. A ventilator is operated with the processor to perform a recruitment procedure. A system for providing mechanical ventilation to a patient includes a mechanical ventilator configured for pneumatic connection to a patient in order to deliver medical gas to the patient. A peripheral system is configured to provide medical assistance to the patient and the peripheral system produces a signal indicative of the operation of the peripheral system. A processor is communicatively connected to the mechanical ventilator in the peripheral system. The processor receives the signal from the peripheral system and calculates a first score from the signal. The processor aggregates the first score into a derecruitment score and compares the derecruitment score to a predetermined threshold. The processor operates the mechanical ventilator to provide a recruitment procedure to the patient.

19 Claims, 3 Drawing Sheets

(56) References Cited

U.S. PATENT DOCUMENTS

| | | |
|---|---|---|
| 2003/0176774 A1 | 9/2003 | Hickle et al. |
| 2004/0118404 A1 | 6/2004 | Wallace et al. |
| 2007/0062533 A1* | 3/2007 | Choncholas et al. .... 128/204.23 |
| 2007/0163584 A1 | 7/2007 | Bohm et al. |
| 2008/0185009 A1 | 8/2008 | Choncholas et al. |
| 2008/0230065 A1* | 9/2008 | Heinonen ................ 128/204.23 |
| 2008/0295839 A1* | 12/2008 | Habashi ................... 128/204.22 |
| 2009/0055735 A1 | 2/2009 | Zaleski et al. |
| 2009/0241957 A1* | 10/2009 | Baker, Jr. ................. 128/204.23 |
| 2009/0272381 A1* | 11/2009 | Dellaca et al. ........... 128/204.23 |
| 2010/0051026 A1* | 3/2010 | Graboi ..................... 128/203.12 |
| 2010/0224192 A1* | 9/2010 | Dixon et al. ............. 128/204.23 |
| 2012/0010520 A1* | 1/2012 | Brochard et al. ............. 600/538 |
| 2012/0037159 A1* | 2/2012 | Mulqueeny et al. ..... 128/204.23 |

OTHER PUBLICATIONS

Magnusson, L. et al. New concepts of atelectasis during general anaesthesia. The Board of Management and Trustees of the British Journal of Anaesthesia, (2003), vol. 91, No. 1, pp. 61-72.

* cited by examiner

SYSTEM AND METHOD OF AUTOMATED LUNG RECRUITMENT MANEUVERS

BACKGROUND

The present disclosure is related to the field of respiratory support and therapy. More specifically, the present disclosure is related to a system and method of automated lung recruitment maneuvers.

Mechanical ventilation is a commonly accepted medical practice in the treatment of individuals experiencing respiratory problems. The patient may be too weak from disease and/or sedation from an anesthetic agent to initiate a respiratory cycle under his own power. In these instances, mechanical ventilatory assistance is provided by ventilator.

Generally, lung function can be improved by recruitment, wherein the increases in lung volume translate into increased surface area for gas exchange, versus derecruitment, wherein lung volume and surface area for gas exchange is reduced. Derecruitment in the lungs can be a sign of more severe physiological conditions. If derecruitment is detected, the condition can sometimes be reversed using a variety of techniques directed to promoting recruitment of lung volume to recover the lost capacity for effective gas exchange.

BRIEF DISCLOSURE

A method of evaluating a patient for need of a recruitment procedure includes monitoring at least one derecruitment factor with a processor. The processor calculates a score for the at least one derecruitment factor. A derecruitment score is aggregated from the calculated score. The processor compares the derecruitment score to a recruitment threshold. The processor operates a ventilator to perform a recruitment procedure.

A non-transient computer readable medium is programmed with computer readable code that upon execution by the processor, causes the processor to monitor at least one derecruitment event. The processor calculates a score for the at least one such non-physiological parameter or event. The processor aggregates the scores for the at least one derecruitment event. The aggregated scores are compared to a predetermined derecruitment threshold. When the aggregated scores exceed the predetermined derecruitment threshold, the processor operates a mechanical ventilator to provide a recruitment procedure to a patient.

A system for providing mechanical ventilation to a patient includes a mechanical ventilator configured for pneumatic connection to a patient in order to deliver medical gas to the patient. A peripheral system is configured to provide medical assistance to the patient and produces a signal indicative of the operation of the peripheral system. A processor is communicatively connected to the mechanical ventilator, the physiological sensor, and the peripheral system. The processor is further communicatively connected to a computer readable medium configured with a computer readable code that upon execution by the processor causes the processor to perform functions. The processor receives the signal from the peripheral system sensor. The processor calculates a first score from the signal. The processor receives the physiological value from the physiological sensor and calculates a second score from the physiological value. The processor aggregates the first score and the second score into a derecruitment score. The processor compares the derecruitment score to a predetermined threshold and if the derecruitment score exceeds the predetermined threshold, the processor operates the mechanical ventilator to provide a recruitment procedure to the patient

DETAILED DESCRIPTION

Figure 1:
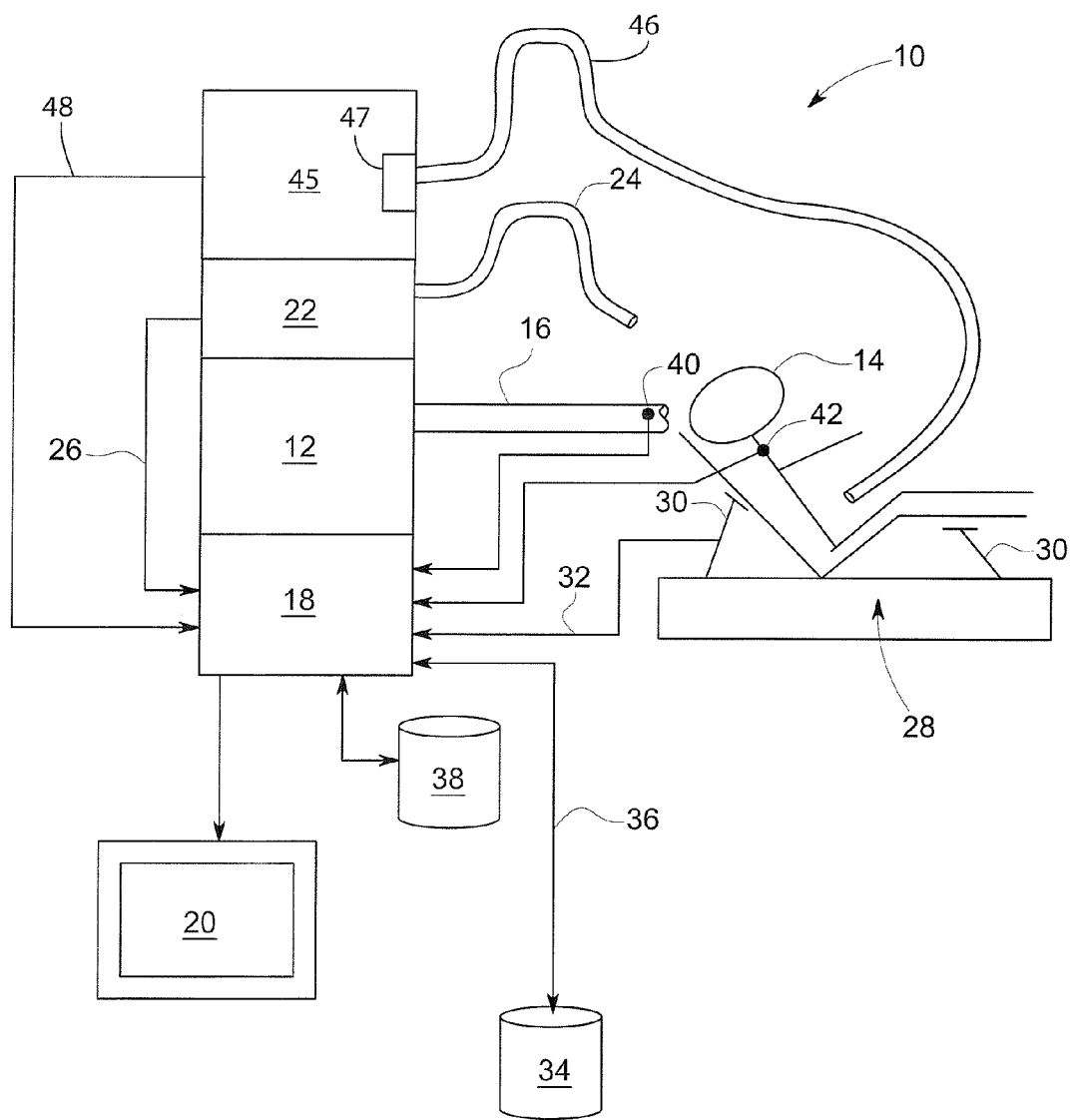
FIG. 1 is a schematic diagram of an exemplary respiratory support system.

FIG. 1 is a schematic diagram of an exemplary embodiment of a respiratory support system 10. The system 10 includes a mechanical ventilator 12. The mechanical ventilator 12 provides medical gas to a patient 14 through a breathing circuit 16. The medical gas supplied to the patient 14 by the ventilator 12 may be any of a variety of known medical gases that include, but are not limited to, one or more of oxygen, nitrogen, nitrous oxide, helium, heliox or others. Additionally, the mechanical ventilator 12 may also deliver vaporized medication to the patient such as anesthetic agent or other drugs.

A processor 18 is communicatively connected to the mechanical ventilator. In one embodiment, the processor 18 is an integral part with the mechanical ventilator 12 and in an alternative embodiment, the processor 18 is part of a stand-alone device that may be, but is not limited to, a personal computer or hand-held device. In an embodiment wherein the processor 18 is part of a separate or mobile device, this embodiment may be particularly useful for monitoring a patient during periods of transition between rooms and medical equipment. The processor 18 is, in any embodiment, communicatively connected to the mechanical ventilator 12, such that the processor 18 is able to receive information from the mechanical ventilator 12 as described in further detail herein and is able to control or operate or at least modify the control or operation of the mechanical ventilator 12, such as disclosed in further detail herein.

The processor 18 is communicatively connected to a graphical display 20. The graphical display 20 is configured to visually present information to a clinician as disclosed in further detail herein. As with the processor 18, the graphical display 20 may be an integral part of a single unit that includes the processor 18 and mechanical ventilator 12. In an alternative embodiment, the graphical display 20 is part of a stand alone device that is either integrated with, or communicatively connected to, the processor 18.

The processor 18 is further at least communicatively connected to a variety of peripheral systems. These peripheral systems include components of the mechanical ventilator 12 and/or otherwise separate devices that are used in the monitoring and treatment of the patient 14. One example of a peripheral system is a suction machine 22. The suction machine 22 is connected to a suction catheter 24 that is used to perform a suction procedure on the patient's lungs and/or airway. A suction machine 22 is one therapeutic tool available to a clinician in order to remove a buildup of fluid, mucous, or other substances within the lung and/or airway of the patient 14. The suction machine 22 is communicatively connected to the processor 18. The suction machine 22 provides a suction signal 26 to the processor 18 to indicate that a suction procedure has been performed.

An alternative peripheral system is that of bed 28. The bed 28 is an electro-mechanical bed that may be adjusted to provide comfort and/or therapeutic support to the patient 14. Such adjustments to the position or angle of the bed may be to elevate the feet of the patient 14, or to incline the patient's torso to a generally seated position. The bed 28 may be a surgical bed that can be articulated and inclined to facilitate laprascopic or abdominal robotic surgeries. One such articulation includes tilting the bed 28 in a Trendelenburg position where the feet of the inclined patient 14 are elevated above the head. Bed sensors 30 detect the position and/or angle of the configuration of components of the bed 28 and provide a bed signal 32 from the bed sensors 30 to the processor 18 indicative of the detected position and/or angle.

Another peripheral system is that of a gas insufflation machine 45. The gas insufflation machine adds gases (such as carbon dioxide) into the abdomen of patient 14 through the tube 46. The gas insufflation machine 45 further regulates the gas pressure introduced into the patient's abdomen that distends the abdomen for laprascopic or robotic surgeries to be conducted within the closed abdominal cavity. Insufflation sensors 47 detect the gas delivery and distending pressure of the abdomen of the patient 14 and provide a insufflation signal 48 to the processor 18 indicative of the detected abdominal insufflation.

In a still further embodiment, the processor 18 is communicatively connected to an electronic medical record (EMR) 34 of the patient 14. The EMR 34 may be stored at a location remote from the processor 18, such as a centralized hospital information system or server. The processor 18 may be communicatively connected to the EMR 34 through a hospital intranet, or the Internet using a wired or wireless data communication platform. The EMR 34 can be a peripheral system itself or can serve as an aggregator of information from a variety of peripheral systems used with the patient. These peripheral systems may be imaging systems, surgery systems, food service systems, or other monitoring or treatment systems in the clinical setting as would be recognized as applicable to the presently disclosed systems and methods by one of ordinary skill in the art. Exemplarily, imaging information such as CT scans or PET scans can perform imaging of the lungs that can indicate derecruitment, the detection of such an event, indicated in the EMR can be provided to the processor 18. The EMR 34 may be updated by a clinician or clinicians that perform various tasks or procedures on the patient 14 and record the information in the EMR 34. Therefore, the processor 18 is able to obtain an EMR signal 36 that is indicative of events involving one or more of a variety of other peripheral systems that are not immediately located with the patient 14 and the mechanical ventilator 12.

Finally, the mechanical ventilator 12 itself may include a variety of peripheral systems as used in the present disclosure. The peripheral systems may be additional features of the mechanical ventilator 12 such as particular functions or modes of operation. The mechanical ventilator 12 provides a ventilator signal to the processor 18 that is indicative of the initiation or detection of these features or processes. Exemplary, but not limiting, features and processes in the mechanical ventilator may be indications of a switch between bag and vent modes on the mechanical ventilator 12, an indication of a delivery of 100% oxygen to the patient 14, an indication of a change in, or the elimination of, PEEP therapy provided by the mechanical ventilator 12 to the patient 14, or a detection that the breathing circuit 16 has been disconnected from the patient 14.

Thus, the peripheral systems as described above with respect to the respiratory support system 10 include a wide variety of devices, functions, or processes that may be performed in the monitoring and treatment of the patient 14. The signal provided by the peripheral systems to the processor 18 may be categorized as being indicative of particular events in the monitoring or treatment of the patient 14. As will be described in further detail below, events indicated by the peripheral systems may be related to or be indicative of an increased risk for lung derecruitment. The monitoring of these events by the processor 18 will be explained in further detail herein.

The processor 18 is connected to at least one, if not a plurality of physiological sensors. The physiological sensors may be connected directly to the processor 18 such that the sensor provides physiological sensors to the processor 18. Alternatively, the physiological sensors are components of a separate monitoring system, such as a patient monitoring system (not depicted) that in turn provides the acquired physiological signals to the processor 18. The respiratory support system 10 is depicted with two exemplary physiological sensors. A gas analyzer 40 is disposed in the breathing circuit 16 in order to analyze the concentration of the component gases expired by the patient 14. Additional physiological parameters that may be obtained from the mechanical ventilator 12 or sensors associated therewith include a patient tidal volume and patient functional residual capacity (FRC). As exemplarily shown through these physiological parameter values from the mechanical ventilator, the physiological parameters may be parameters that are measured directly from the patient, or may be derived parameters, such as FRC, that are calculated in known manners based upon a variety of measured values.

An alternative physiological sensor is that of biopotential sensor 42 that is affixed or otherwise attached to the patient 14. The biopotential sensor 42 may be any of a variety of biopotentials, including electrocardiogram (ECG), electromyogram (EMG), electroencephalogram (EEG), or electrical impedance tomography (EIT); however, these are not intended to be limiting on the types of biopotentials that may be monitored as physiological parameters in embodiments disclosed herein. Additionally, alternative sensors to the biopotential sensor 42 may measure physiological parameters from the patient 14. Exemplarily alternative sensors may include blood oxygen saturation (SPO2) or non-invasive blood pressure (NIBP), which are known physiological parameters in the field. As will be described in further detail herein, physiological parameters measured by the physiological sensors may be related to, or indicative of an increased risk for lung derecruitment, particularly when analyzed in combination with other physiological parameters or derecruitment events.

The processor 18 is connected to a computer readable medium 38. The computer readable medium 38 may be an integral component with the processor 18 and the mechanical ventilator 12 in the form of computer memory. Alternatively, the computer readable medium 38 may be located remotely to the processor 18 and is only communicatively connected such as through the Internet or a hospital intranet. In these embodiments, the computer readable medium 38 may be a remotely located server.

In still further embodiments, the computer readable medium 38 may be a portable form of computer readable media such as a CD ROM or flash memory. These descriptions of computer readable media are intended to be merely exemplary, and not intended to be limiting on the scope of non-transient computer readable media that may be used in connection with the embodiments of the systems and methods as disclosed herein.

Figure 2:
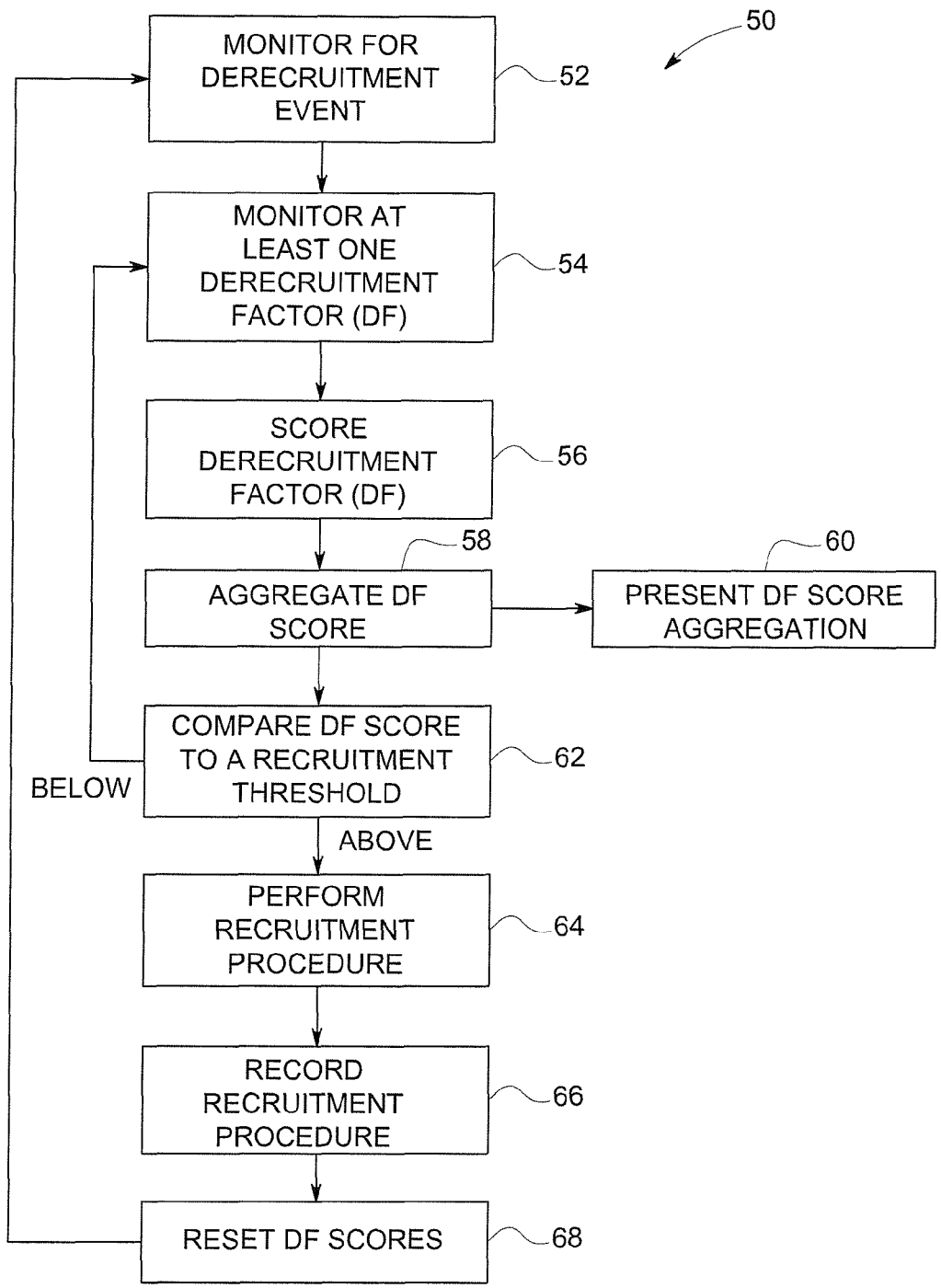
FIG. 2 is a flow chart depicting an embodiment of a method of automated recruitment procedures.

FIG. 2 is a flow chart depicting the steps of an embodiment of a method 50 of automatedly providing recruitment procedure therapy to a patient. The method 50 may be performed by the coordinated operation of the components of a system, exemplarily the respiratory support system 10 of FIG. 1. Alternatively, the embodiments of the method 50 may be performed by a computer processor that is executing computer readable code stored on a non-transient computer readable medium.

The method 50 begins with monitoring the peripheral systems for a derecruitment event at 52. As noted above, notifications of particular events received from peripheral systems are indicative of an increased risk for patient derecruitment. These events include many of the events identified above with respect to the peripheral systems and include, but are not limited to: suction procedures, adjustment of the bed position or angle, insufflation of the abdomen, switching of the ventilator from bag to vent mode, inadvertent disconnection of the breathing circuit from the patient, the delivery of 100% oxygen to the patient, or a change in or the elimination of PEEP therapy delivered to the patient. The detection of one or more of these events at 52 causes the method to proceed to monitor at least one derecruitment factor (DF) at 54.

The derecruitment factors (DF) are those physiological parameters that are measured from the patient. As noted above, these derecruitment factors include, but are not limited to, an analysis of expired gases including gas concentration, patient tidal volume, patient airway pressure (Paw) or FRC, ECG, NIBP, or SPO2.

The at least one monitored derecruitment factor is scored at 56 in order to weight a risk of patient lung derecruitment indicated by the at least one monitored derecruitment factor. The score for the derecruitment factor may be provided by a frequency distribution or fuzzy logic that rates the derecruitment risk to an associated value based upon the monitored value of the derecruitment factor. In a merely exemplary embodiment, the scores of 1, 2, and 3 may be respectively assigned to derecruitment factor values that indicate a low, medium, or high risk of patient derecruitment.

Alternatively, the derecruitment factor (DF) score at 56 may be in the form of a percentage or likelihood of patient derecruitment as indicated by the value of the monitored derecruitment factor. This percentage or risk may further take into account any trends or changes in the derecruitment factor value since the detected derecruitment event. In one embodiment, a length of time since the derecruitment event is taken into account in the DF score. Therefore, the DF score may vary over time as not only the instantaneous DF value changes, but the trending of the DF value changes over time as well. The particular score and weights assigned to specific DF values may be informed by empirical research and data mining regarding monitored physiological data in patients that experience derecruitment.

At 58, the DF scores are aggregated. This aggregation of the DF scores can embody different forms of aggregation depending upon the particular embodiment of the method 50 that is being implemented. If only a single derecruitment factor is being monitored, then the aggregation of the DF score may adjust the DF score from 56 to account for previously calculated DF scores. Alternatively, if more than one derecruitment factor is monitored at 54, then the aggregation of the DF scores 58 is a summation, weighted summation, or average of the DF scores assigned to the plurality of monitored derecruitment factors.

In an embodiment, the aggregated DF scores from 58 are presented at 60 on a graphical display. The presented aggregated DF score may serve as a prompt or an indication to an attending clinician, such as a doctor or a nurse, that provides a generalized evaluation of a risk that the patient will experience derecruitment. Therefore, in an embodiment, a properly notified clinician may respond to the presented aggregated DF score at 60 by manually initiating a recruitment procedure.

In the automated embodiment, as disclosed herein at 62, the aggregated DF score is compared to a predetermined recruitment threshold. The predetermined recruitment threshold may be stored on a computer readable medium, such as read only memory or flash memory that is associated with the processor. The predetermined recruitment threshold is a value in the same format as the DF scores. If the DF scores are numerical values or risk percentages, then the predetermined recruitment threshold is the same format as the DF score. The predetermined recruitment threshold is a threshold value that is representative of the conditions when a recruitment procedure should be performed. The predetermined recruitment threshold may vary depending upon the derecruitment event that is detected at 52. This use of a variety of predetermined recruitment thresholds recognizes that some of the monitored derecruitment events may carry with them a higher risk of patient derecruitment than other events, and therefore, a lower aggregated DF score may justify an automated intervention on behalf of the patient.

As represented by the decision arrows extending from 62, if the DF score is below the predetermined recruitment threshold, then the method may return to 54 to continue to monitor the at least one derecruitment factor. If, however, the aggregated DF score is above the predetermined derecruitment threshold, then the method 50 proceeds to perform a recruitment procedure at 64.

In a still further embodiment, the DF scores are used to form a feature vector for a classification algorithm or classifier which chooses between two classes. One class is representative of derecruitment and another representative of no derecruitment. Classifiers used in this embodiment may include a Gaussian Bayesian classifier or a neural net. Either of these classifiers define a complex threshold with a hyperplane decision boundary. By relating the DF scores as vectors, the normal distributions for the classes of derecruitment or no derecruitment can take the form of a plane or surface, rather than a one dimensional predetermined derecruitment threshold value.

In an embodiment, the performance of the recruitment procedure is an automated function and a processor that is forming the monitoring and analysis of the derecruitment factors to further operation a mechanical ventilator to perform a recruitment procedure.

A variety of recruitment procedures may be performed by a mechanical ventilator under the automated operation of a processor in accordance with an embodiment of the method. A recruitment procedure may be performed over the course of a single respiratory cycle by providing an increased volume of medical gas to the patient. In an alternative form of recruitment procedure performed over a plurality of respiratory cycles, positive end expiatory pressure (PEEP) is gradually applied to the patient. The additional expiratory pressure can promote lung volume recruitment by keeping additional lung volume open at the end of the patient's expiration. As this additional lung volume does not recollapse upon expiration, the patient's overall airway resistance is reduced and more of the alveoli are opened, promoting additional lung efficiency and further recruitment.

In a still further example of a recruitment procedure, one or more substances are added to the medical gas that are delivered to the patient. In one embodiment, a surfactant is nebulized into the medical gas. The surfactant reduces the surface tension of the alveoli and helps the collapsed alveoli to open with less pressure, which causes more alveoli to open. These disclosed techniques for lung volume recruitment procedures are intended to be merely exemplary and are not intended to be limiting on the scope of the recruitment procedures that may be automatedly performed at 64.

After the lung volume recruitment procedure is automatically performed by the mechanical ventilator at the operation of the processor, a record is made of the recruitment procedure at 66. This record may be recorded on a patient's electronic medical record (EMR) by the processor. The recording of the recruitment procedure may indicate a time of the procedure, an indication of the procedure performed, physiological response to the procedure, and any other additional information as would be deemed relevant by one of ordinary skill in the art.

After the recruitment procedure has been recorded at 66, the method may reset the DF scores at 68. This is performed in order to reset the method. As a recruitment procedure has just been performed at 66, the method 50 is able to return to 52 and monitor for a new derecruitment event that would indicate that the therapy provided with the recruitment procedure at 66 has been compromised. The initial scores may be set with a biased value to prevent the recruitment procedures from being repeated too frequently. Alternatively, an elapsed time counter may be started with the last procedure to delay the initiation of a next recruitment procedure.

Figure 3:
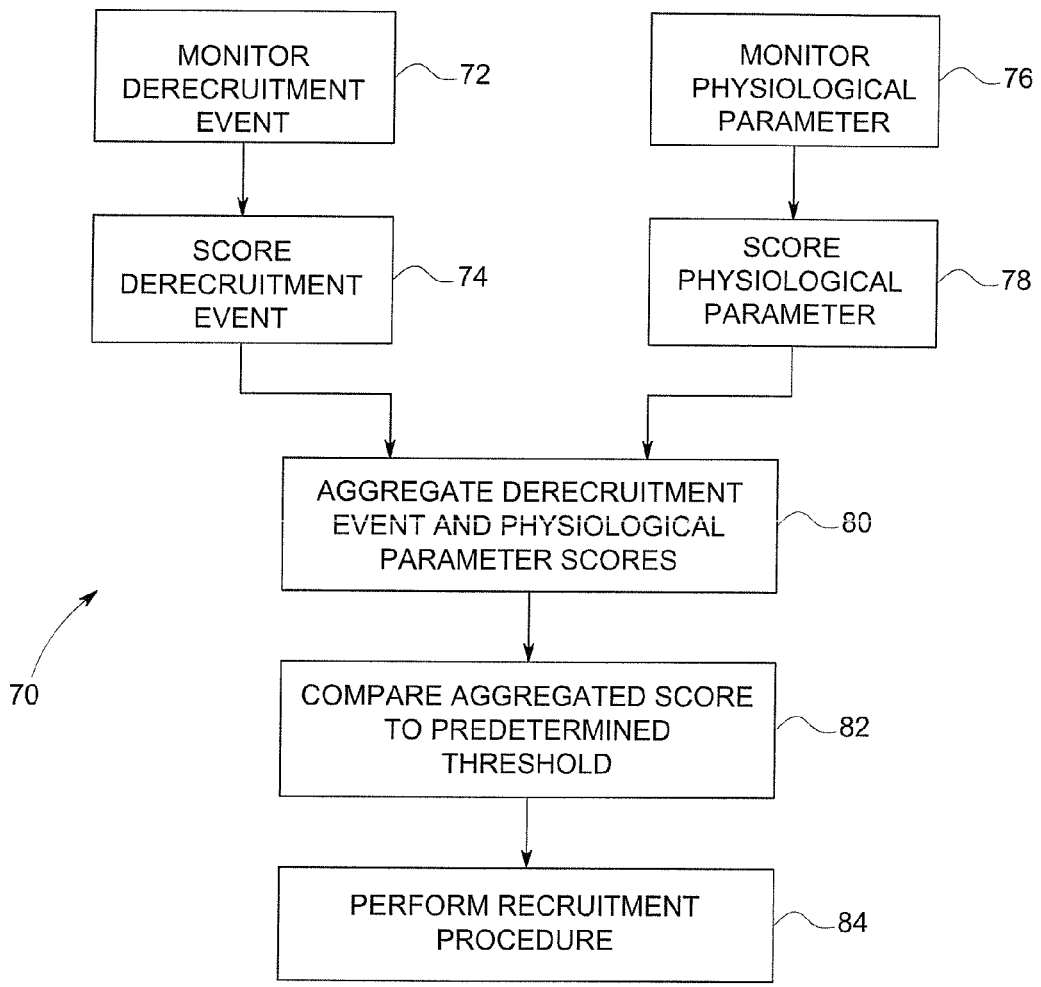
FIG. 3 is a flow chart depicting an alternative embodiment of a method of automated recruitment procedures.

FIG. 3 is a flow chart that depicts an alternative embodiment of a method 70 of an automatedly performed recruitment procedure.

The method 70 monitors at least one derecruitment event at 72. While some embodiments may only monitor a single derecruitment event, in an alternative embodiment, a plurality of potential derecruitment events may be simultaneously monitored. These derecruitment events may include, but are not limited to, events that may be indicated from peripheral systems including suction procedures, bed position or angle adjustments, disconnection of the patient from the breathing circuit, or mechanical ventilator setting changes such as a change between bag and vent modes, the delivery of 100% oxygen, or changes in the delivery of PEEP.

At 74, each of the monitored derecruitment events are given a score. If an event is not detected, then in an embodiment a score of zero or null is assigned until that derecruitment event is detected. Some embodiments rely solely upon the detection of a monitored derecruitment event, independent of any physiological parameters.

In the embodiment depicted in FIG. 3, simultaneous to the monitoring for the derecruitment events, at least one, and alternatively, a plurality of physiological parameters are monitored at 76. These physiological parameters may include a variety of commonly monitored physiological parameters that may be monitored by the mechanical ventilator itself, such as expired gas concentration, patient tidal volume, or patient FRC. Alternatively, the physiological parameters monitored at 76 may include those physiological parameters that are monitored by a patient monitoring device that exemplarily includes oxygen saturation (SPO2), electrocardiogram (ECG), and non-invasive blood pressure (NIBP). The physiological values are intended to be merely exemplarily and not intended to be limiting on the scope of physiological parameters that may be monitored in embodiments of the method 70.

Similar to the derecruitment event, at 78, the monitored physiological parameters are scored. As noted above with respect to the method 50, the physiological parameter scores may represent relative risks of patient derecruitment that are associated with the values of the monitored physiological parameters. In addition to a score based upon each physiological parameter individually, the score for a physiological parameter may further take into account the values of the other monitored physiological parameters or the monitored derecruitment event. Therefore, in some embodiments, the presence of a particular detected derecruitment event may increase or decrease the score attributed to a monitored physiological parameter value. As noted above, in one embodiment, the scores for the physiological parameters provide a weighting to indicate the risk or severity of the measured physiological parameter values. Embodiments may further employ Boolean logic or fuzzy logic in order to assign scores to one or more of the physiological parameter values.

At 80, the derecruitment event scores from 74 and the physiological parameter scores from 78 are aggregated to provide an aggregated derecruitment score. The aggregation of the scores may be a simple summation. Alternatively, the weighting of the importance or value of the derecruitment event scores and the physiological parameter scores in the analysis of patient derecruitment risk may be performed at 80 during the aggregation of the scores.

Once an aggregated score is calculated at 80, the aggregated score is compared to a predetermined derecruitment threshold value at 82. The predetermined derecruitment threshold value may be stored at a storage medium that is accessible to a processor that performs the steps of the method 70. In one embodiment, the predetermined derecruitment threshold is a defined value, that is indicative of a derecruitment risk at which automated intervention is warranted. This predetermined derecruitment threshold may be institutionally established based upon the current understanding or art. Alternatively, the predetermined derecruitment threshold may be established by a clinician, or may be a default parameter established in the commercial embodiment of the method.

Alternatively, the predetermined threshold may be one of a plurality of predetermined thresholds that is selected based upon the specific derecruitment events and physiological parameters that are monitored, and also those that are detected.

The comparison of the aggregated derecruitment score to the predetermined derecruitment threshold at 82 provides an indication if the patient's condition warrants an automated intervention in the form of a recruitment procedure. If the predetermined derecruitment threshold is exceeded by the aggregated derecruitment score, then a recruitment procedure is performed at 84. Exemplary forms of the recruitment procedures that may be performed at 84 are described above with respect to method 50.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A method of providing a recruitment procedure to a patient receiving respiratory support from a mechanical ventilator, the method comprising:

monitoring, with a processor, at least one peripheral system for a derecruitment event;

monitoring at least one physiological sensor for at least one derecruitment factor with the processor;

calculating a derecruitment event score, with the processor, for the at least one derecruitment event;

calculating a derecruitment factor score, with the processor, for the at least one derecruitment factor;

aggregating the derecruitment event score and the derecruitment factor score into a derecruitment score indicative of a risk of lung derecruitment;

comparing, with the processor, the derecruitment score to a recruitment threshold stored on a computer readable medium; and operating a ventilator with the processor to initiate performance of a recruitment procedure based upon the comparison of the derecruitment score to the recruitment threshold.

2. The method of claim 1, further comprising:
receiving a signal with the processor from the at least one peripheral system; and
receiving a signal with the processor from the at least one physiological sensor;
wherein the derecruitment event score for the at least one derecruitment event is calculated with the processor from the signal from the at least one peripheral system; and
wherein the derecruitment factor score for the at least one derecruitment factor is calculated with the processor from the signal from the at least one physiological sensor.

3. The method of claim 1, further comprising:
identifying a monitored derecruitment event; and
based upon the identified derecruitment event, selecting the at least one derecruitment factor to monitor.

4. The method of claim 1, wherein calculating the score of the at least one derecruitment event and the score of the at least one derecruitment factor further comprises weighting the scores based upon a correlation strength between the derecruitment event or derecruitment factor and a risk of patient derecruitment.

5. The method of claim 1, wherein calculating the score of the at least one derecruitment event and the at least one derecruitment factor further comprises weighting the scores based upon an elapsed time since the detection of the derecruitment event or the derecruitment factor.

6. The method of claim 1, wherein calculating the score of the at least one derecruitment event and the score of the at least one derecruitment factor further comprises weighting the scores based upon a trend in the monitored at least one derecruitment event or the at least one derecruitment factor.

7. The method of claim 1, wherein the at least one derecruitment event is a suction event and the at least one derecruitment factor is airway pressure.

8. The method of claim 1, wherein the at least one derecruitment event is a change in orientation of a bed of the patient.

9. The method of claim 1, wherein the at least one derecruitment event is an abdominal insufflation.

10. The method of claim 1, further comprising:
presenting on a graphical display a prompt to a clinician to initiate a recruitment procedure;
receiving a signal indicative of the initiation of the recruitment procedure.

11. The method of claim 1, further comprising operating a graphical display to present the derecruitment score.

12. The method of claim 1, further comprising:
recording an indication that the recruitment procedure has been performed; and
resetting the derecruitment score.

13. A non-transient computer readable medium programmed with computer readable code that upon execution by a processor, causes the processor to:
receive at least one signal from a peripheral system;
monitor at least one derecruitment event from the at least one signal from the peripheral system;
calculate a derecruitment event score indicative of a risk of lung derecruitment for the at least one derecruitment event;
receive at least one signal from a physiological sensor;
monitor at least one derecruitment factor from the at least one signal from the physiological sensor;
calculate a derecruitment factor score indicative of a risk of lung derecruitment for the at least one derecruitment factor;
aggregate the derecruitment event score and the derecruitment factor score;
compare the aggregated scores to a predetermined derecruitment threshold; and
when the aggregated scores exceed the predetermined derecruitment threshold, operate a mechanical ventilator to provide a recruitment procedure to a patient.

14. The non-transient computer readable medium of claim 13, wherein the scores for the at least one derecruitment event and the at least one derecruitment factor are weighted based upon a correlation between the derecruitment event or derecruitment factor and a lung derecruitment of the patient.

15. A system for providing mechanical ventilation to a patient, the system comprising:
a mechanical ventilator configured for pneumatic connection to a patient in order to deliver medical gas to the patient;
at least one physiological sensor that measures at least one physiological value;
a peripheral system configured to provide medical assistance to the patient and the peripheral system produces a signal indicative of the operation of the peripheral system;
a processor communicatively connected to the mechanical ventilator, the physiological sensor, and the peripheral system, the processor further communicatively connected to a computer readable medium configured with computer readable code that upon execution by the processor, causes the processor to:
receive the signal from the peripheral system,
calculate a first score from the signal;
receive the physiological value from the physiological sensor;
calculate a second score from the physiological value;
aggregate the first score and the second score into a derecruitment score;
compare the derecruitment score to a predetermined threshold; and
if the derecruitment score exceeds the predetermined threshold, operate the mechanical ventilator to provide a recruitment procedure to the patient.

16. The system of claim 15, further comprising a graphical display and wherein the processor operates the graphical display to present the derecruitment score.

17. The system of claim 15, wherein if the derecruitment score exceeds the predetermined threshold, the processor operates the graphical display to present a prompt for a clinician to initiate a recruitment procedure, and the processor receives a signal indicative of initiating a recruitment procedure before operating the mechanical ventilator to provide a recruitment procedure to the patient.

18. The system of claim 15, wherein the processor compares the first score to a predetermined threshold, and upon exceeding the predetermined threshold, the processor receives the physiological value from the physiological sensor.

19. The system of claim 18, wherein the signal is a signal indicative of a suction procedure, and the physiological value is an airway pressure.

* * * * *